United States Patent [19]

Carroll et al.

[11] Patent Number: 4,933,279

[45] Date of Patent: Jun. 12, 1990

[54] STARCH LIQUEFACTION WITH ALPHA AMYLASE MIXTURES

[75] Inventors: John O. Carroll, Norwalk; Timothy R. Swanson, Brookfield Center; Philip C. Trackman, Bethel, all of Conn.

[73] Assignee: Novo Industri A/S, Bagsvaerd, Denmark

[21] Appl. No.: 294,813

[22] Filed: Jan. 9, 1989

Related U.S. Application Data

[63] Continuation-in-part of Ser. No. 883,566, Jul. 9, 1986, abandoned.

[51] Int. Cl.$^5$ .................... C12N 9/28; C12P 19/14; C12R 1/07; C12R 1/10
[52] U.S. Cl. ........................................ 435/42; 435/99; 435/202; 435/252.4; 435/836

[58] Field of Search ............... 435/42, 99, 202, 836, 435/252.4

[56] References Cited

U.S. PATENT DOCUMENTS 2,891,869  6/1959  Langlois ............................. 435/96
4,642,288  2/1987  De Miguel et al. ................. 435/99

Primary Examiner—Herbert J. Lilling
Attorney, Agent, or Firm—Morris Fidelman; Franklin D. Wolffe

[57] ABSTRACT

A mixed enzyme product comprising a mixture of the alpha-amylase from *Bacillus licheniformis* and the alpha-amylase from *B. stearothermophilus*, said mixture containing from 10%–90%, preferably 25%–90%, more preferably 25%–75% by activity as NU/g DS of the *Bacillus licheniformis* enzyme and is usable with advantage for liquefaction of starch or starchy grains.

7 Claims, No Drawings

STARCH LIQUEFACTION WITH ALPHA AMYLASE MIXTURES

This application is a continuation-in-part of Ser. No. 883,566 filed Jul. 9, 1986, now abandoned.

BACKGROUND OF THE INVENTION

For the decade prior to the decade hereof, glucose/fructose mixtures manufactured from corn starch constituted an ever-growing segment of the U.S. sugar industry. This segment of the sugar industry has grown to such size as to demand substantial quantities of the starch converting enzymes which generate the glucose/fructose mixtures. In particular, industrial usage of thermally stable alpha-amylase to hydrolyze the corn starch has grown into a market worth several million dollars per annum to suppliers of the enzyme.

Heretofore, the alpha-amylase from *Bacillus licheniformis*, (e.g., TERMAMYL ®) was the thermally stable enzyme of choice. As of the date hereof, however, the art has been offered an opportunity to shift to the thermally stable alpha-amylase elaborated by *Bacillus stearothermophilus* (e.g., THERMOLASE TM). For background on this alpha-amylase, reference is made to Pat. Nos. 2,695,863 and 4,284,722.

The *B. stearothermophilus* enzyme has certain advantages over the *Bacillus licheniformis* enzyme, notably, a higher specific activity, a lower pH optimum, and a modest improvement in dextrose yield. Unfortunately, liquefying starch with the *B. stearothermophilus* enzyme causes appearance of significant levels of sediment in the glucose syrup unless a high dosage level of the *B. stearothermophilus* enzyme is employed. Costs of removing the sediment from the syrup largely negate the advantages offered by this enzyme.

Analysis of the sediment generated in the syrup by use of the *B. stearothermophilus* alpha-amylase at normal dosage levels indicates that the sediment constitutes a polysaccharide, which polysaccharide may be complexed with lipid and protein. Apparently some component in the starch is poorly hydrolyzed by this alpha-amylase, since this sediment problem can be resolved by increasing dosage of the alpha-amylase substantially. The possibility exists, therefore, that treatment of either the starch or the dextrin with small amounts of some enzyme effective against the sediment forming fraction, might resolve the sediment problem.

Liquefying starch at pH 6.0–6.5 with normal dosage levels of the *Bacillus licheniformis* enzyme does not generate undue levels of sediment. However, when liquefying with the *Bacillus licheniformis* enzyme at pH 5.5–6.0 excessive sediment is also generated (and otherwise relatively poor liquefaction results).

The below-tabulated test results from laboratory scale comparative studies wherein the liquefaction was simulative of industrial usage circumstances and standard saccharification practices were followed illustrates the degree to which sediment appears at different liquefaction pH and enzyme dosage.

| Liquefaction Enzyme | Sediment Volume (% vol/vol) Liquefaction pH | | | |
|---|---|---|---|---|
| | 5.0 | 5.5 | 5.8 | 6.0 |
| TERMAMYL ® 85 NU/g DS | | 2.5*, ** | 2.0* | 1.5 |
| THERMOLASE TM 50 NU/g DS | 50 | 10 | 7 | 25 |
| THERMOLASE TM 50 NU/g DS | | | 5 | |
| THERMOLASE TM 100 NU/g DS | | | 2 | |

*Accompanied by poor liquefaction results
**At pH 5.5 twice the usual Ca++ level was employed to stabilize the TERMAMYL ®

The activity standard NU (which is an abbreviation of NOVO alpha-amylase unit) is the amount of enzyme which breaks down 5.26 mg of dissolved starch per hour at 37° C., pH 5.6 and 0.0043M of $Ca^{++}$ over a 7–20 minute reaction time. The analytical method AF-9 is available on request to NOVO INDUSTRI A/S, DK-2880 Bagsvaerd, Denmark. At the starch liquefaction operating range of 90°–110° C., the THERMOLASE TM has been found to be more active than the TERMAMYL ® by a factor of about 1.7. The test study results tabulated above which compared TERMAMYL ® and THERMOLASE TM at starch liquefaction temperatures was an equal activity level study i.e., 50 NU/g DS of THERMOLASE TM is as effective as 85 NU/g DS of TERMAMYL ® at the conditions of use.

Surprisingly, liquefying starch at pH 5.5–6.0 with a mixture of the *Bacillus licheniformis* alpha-amylase and the *B. stearothermophilus* alpha-amylase eliminated the sediment problem without harm to liquefaction results.

SUMMARY OF THE INVENTION

Briefly stated, this invention provides a mixed alpha-amylase comprising 10°–90° of the *Bacillus licheniformis* alpha-amylase, 10–90% of the *B. stearothermophilus* alpha-amylase all by NU activity; 25–75% constitutes one preferred range and 25–50% another. Improvement in sediment level has been found with mixtures containing from 10%–90% *Bacillus licheniformis* alpha-amylase. An about 2:1 (of 66%, 34%) ratio of the *Bacillus licheniformis* to the *B. stearothermophilus* amylase constitutes a preferred embodiment of this invention.

In practice of this invention, an enzyme dosage not exceeding about 80 NU/g, the range of 20–80 NU/g DS is preferred.

The process of this invention follows prior art teachings for starch liquefaction: i.e., jet cooking a 20–40% starch slurry at 100°–115° C. for one to sixty minutes, preferably one to ten minutes, followed by reducing the temperature to 80°–100° C. and holding at 80°–100° C. for 30–180 minutes, after which the solution of liquefied starch is stable against starch retrogradation and may be cooled safely. These liquefaction conditions are suggested by U.S. Pat. No. 3,912,590. On the date hereof, standard industry practices for starch liquefaction are: 35% DS (dry substance) slurry, jet cooking at 105° C. for five minutes (of primary liquefaction) followed by holding at 95° C. for ninety minutes (of secondary liquefaction).

The importance of the pH at which liquefaction takes place is not emphasized in U.S. Pat. No. 3,912,590. In practice of the invention of U.S. Pat. No. 3,912,590, pH 6.0–6.5 was employed, such being optimum for the *Bacillus licheniformis* enzyme. The more advantageous pH range of pH 5.5–6.0 may be used with the alpha-amylase from *B. stearothermophilus* and this range pH 5.5–6.0 is employed in preferred practice of this invention.

DISCUSSION OF THE INVENTION

As has already been pointed out, practice of this invention is keyed to starch liquefaction employing a jet cooking step at 100°–110° C. for one to ten minutes with a mixed enzyme. The discussion of enzyme characteristics which follows is strictly within the context of the above stated process parameters for starch liquefaction, and is largely within the context of practices followed by the high fructose syrup industry. However, it should be appreciated that the discussion which follows applies as much to liquefaction of grains and also to liquefaction of starch for purposes other than production of high fructose syrups, and practice of this invention for conduct of such liquefactions is, of course, contemplated.

A substantial source of difficulty for the art always has been pH, namely, at what pH level should the liquefaction be conducted. Starch, as such, slurried for the starch liquefaction process is at pH 3.0–5.0. Most grain slurries directly liquefied (such being employed for brewing, distilling and fuel ethanol processes) have a natural pH of 5.0–6.0 but contain significant buffering capacity. The alpha-amylase from *Bacillus licheniformis* (e.g., TERMAMYL®), is best used at a pH 6.0–6.5. When this enzyme is employed at a pH of below 6.0, liquefaction results deteriorate sharply in some proportion to the pH level. In addition, small but significant quantities of by-products, principally maltulose are produced when this enzyme is employed at about pH 6.2 or higher.

In the high fructose syrup industry, therefore, pH of the starch slurry was adjusted upward to pH 6.0–6.5 before liquefaction with the *Bacillus licheniformis* alpha-amylase, thereby introducing significant ash into the liquefied starch, which ash must be removed e.g., by ion exchange, during the course of the overall process. Also, the grains mashed for brewing, distilling and fuel ethanol processes contain significant buffering capacity, and as a result, the adjustment required to raise their natural pH 5.0–6.0 level to a liquefying level pH 6.0–6.5 contributes a disadvantageously large ash load to the mash.

The *B. stearothermophilus* alpha-amylase can operate well at pH 5.5–6.0. When starch liquefaction is conducted in this pH range, maltulose formation is eliminated, color and organic acid formation are reduced. Use of this alpha-amylase offers the art other advantages as well, notably a modest improvement in the ultimate dextrose yield. However, as has already been pointed out, glucose syrups made from starch liquefied with 40–80 NU/g dry starch of the *B. stearothermophilus* alpha-amylase possess a high level of sediment, and, therefore, filter poorly.

To repeat, syrups made with normal proportions of the *Bacillus licheniformis* alpha-amylase, e.g., 75 NU/g DS at pH 6.0–6.5 do not suffer from the sediment difficulty. Syrups made by liquefying starch with this enzyme at the lower pH 5.5–6.0 contains some sediment in excess, and otherwise liquefaction results deteriorate.

Surprisingly, syrups made at pH 5.5–6.0 with normal enzyme proportions that are mixtures of these two alpha-amylases in 10%–90% *Bacillus licheniformis* alpha-amylase content range by NU/g DS exhibit a far lower level of sediment, the sediment proportion being at about the acceptably low level produced by conventional TERMAMYL® pH 6.0–6.5 liquefaction practices. Since liquefaction results from the *Bacillus licheniformis* enzyme falls off very rapidly when pH decreases below 6.0, a substantial degree of synergism must exist.

The inventors hereof postulate that differences in enzyme specificity and action pattern generate the reduction in sediment formation.

Starch is formed of large complex molecules (mol. wt. > 1 Million Daltons). It is envisioned that two alpha-amylases preferentially attack different parts of the starch molecule, each attacking most rapidly at sites less preferred and/or attacked more slowly by the other, and, thereby, each enzyme quickly releasing fragments more susceptible to immediate attack by the other enzyme. The starch molecule is known to possess both amorphous regions and regions of high crystallinity. The crystalline regions are more resistant to hydrolysis than the amorphous regions, but become relatively more accessible to attack once bonds are broken in the neighboring amorphous regions. Then as crystalline regions are disrupted, more hydrolytic sites are exposed.

Liquefaction is essentially the endo attack of an alpha-amylase on the alpha 1,4 bonds of the glucose polymer chains, which significantly lowers the viscosity of the gelatinized starch.

As is well known, the liquefaction process employed in industrial practice is divided into two main steps: primary liquefaction and secondary liquefaction (dextrinization). For primary liquefaction the starch slurry is heated to 105° C. almost instantly by a jet cooker, and after about five minutes, the liquefied starch solution is cooled to the holding temperature for dextrinization of about 95° C. When primary liquefaction is carried out at pH 6.0 to 7.0, approximately 90% of the *Bacillus licheniformis* alpha-amylase activity remains. However, with primary liquefaction at pH 5.5–6.0, as little as 50% of the activity remains.

For secondary liquefaction, the remaining enzyme activity is allowed to react further at a holding temperature of 90°–100° C. for 30–180 minutes until a desired Dextrose Equivalent (DE) is obtained. The required DE depends on the intended use of the liquefied starch; glucose syrups, maltose syrups, etc.

At the pH optimum for the *Bacillus licheniformis* enzyme, pH 6.5–7.0, approximately 85% of the original activity remains after secondary liquefaction. At the pH optimum for the *B. stearothermophilus* enzyme of approximately pH 5.8, the activity remaining at the end of secondary liquefaction is 95–100%.

Below reproduced are typical test result measurements of the enzyme activity remaining after liquefaction at 105° C. and 95° C., on 35% DS starch slurry, 40 ppm $Ca^{++}$

| | | LIQUEFACTION | |
|---|---|---|---|
| Enzyme Type | pH | Primary % Remaining | Secondary % Remaining |
| TERMAMYL ® | 7.0 | 92 | 86 |
| 85 NU/g DS | 6.5 | 92 | 85 |
| | 6.0 | | 72 |
| | 5.75 | | 63 |
| | 5.5 | | 43 |
| THERMOLASE ™ | 6.0 | | 74 |
| 50 NU/g DS | 5.75 | | 100 |
| | 5.5 | | 83 |

| | LIQUEFACTION | |
|---|---|---|
| Enzyme Type | pH | Primary % Remaining | Secondary % Remaining |
| | 5.0 | | 34 |

The high sediment levels which result from starch liquefaction with the *B. stearothermophilus* alpha-amylase are not observable in the immediate product of the primary liquefaction. The sediment, as such, might be generated in the dextrin solution during the liquefaction step, but in any event, is present in the saccharified syrup and must be removed therefrom. Apparently, some of the starch fragments generated by liquefaction with the *B. stearothermophilus* enzyme become an insoluble product. Analysis of the sediment indicates presence of carbohydrate, protein and lipid moities. Mention has already been made that when the alpha-amylase from *Bacillus licheniformis* is employed at a pH lower than pH 6.0 more than the usual level of sediment appears in the syrup solution. However, the polysaccharides in the sediment generated from starch by each of the two enzymes at pH 5.5–6.0 are not the same.

Since starch liquefaction with greater than normal enzyme dosages of the *B. stearothermophilus* alpha-amylase reduces formation of sediment, and liquefaction with the *Bacillus licheniformis* enzyme at pH 6.0–6.5 produces low sediment levels, the inventors hereof believe that failure to sever enzymatically hydrolyzable linkages (or set of linkages) in the starch molecule underlies generation of the sediment.

In effort to ascertain at which stage of the liquefaction process the sediment avoiding reactions take place, tests were conducted with a split in the mixed enzyme dose. The *B. stearothermophilus* amylase content was added before conduct of the primary liquefaction, then just before the secondary liquefaction, either the *Bacillus licheniformis* amylase content was added, or more of the *B. stearothermophilus* amylase was added. Excessive sediment levels were found in the ultimate glucose syrups, indicating thereby that the sediment avoiding reactions take place during primary liquefaction, and, therefore, that to control the sediment levels, the enzyme mixture should be present during the primary liquefaction.

Fortuitously, whatever linkages in the starch molecule are crucial in generation of sediment by the *B. stearothermophilus* alpha-amylase must be preferentially attacked by the *Bacillus licheniformis* alpha-amylase. After all, this alpha-amylase is rapidly deactivated at 105° C. at pH below pH 6.0 and use of the *Bacillus licheniformis* enzyme alone at pH 5.5–6.0 causes more sediment to occur in the syrup solution. Moreover, the *B. stearothermophilus* alpha-amylase is not present in the liquefaction at more than normal dosage levels, and may be as little as ⅔ or ½ of the NU/g DS dosage levels that produce high levels of sediment in the syrup solution.

Improved sediment level results have been found for enzyme mixtures throughout the range of 10%–90% for the *Bacillus licheniformis* alpha-amylase, even when primary liquefaction is carried out throughout the range pH 5–8, a pH range that includes pH levels at which one or the other enzyme deactivates at 105° C. with extreme rapidity.

Thus, a 10–90% mixture may be employed with some advantage over the following conditions:

| pH | 5.0–8.0 |
|---|---|
| T °C. | 100–115° C. |
| DS | 20–40 |
| $Ca^{+2}$ | 20–200 ppm |

The enzyme mixture can be best used in the 25–90% NU/g DS *Bacillus licheniformis* alpha-amylase content range contemplated for practice of this invention at the following preferred conditions:

| pH | 5.5–6.0 |
|---|---|
| T °C. | 103–110° C. |
| DS | 32–38 |
| $Ca^{+2}$ | 30–80 ppm |

When using the enzyme mixture within the above listed recommended conditions, no filtration problems for the syrup should occur. Dextrose yields after saccharification will be 0.2–0.4% higher (than with the *Bacillus licheniformis* enzyme alone), using mormal levels of amyloglucosidase—pullulanase saccharification enzymes.

ENZYME DOSAGE

In the enzymology art, the usual progression is first to satisfy concern over whether an enzyme capable of catalyzing the desired reaction can be found. After a suitable enzyme is discovered for some particular reaction, workers in the art direct attention to the details of this reaction, such as yield, and the quantity of enzyme required and, of course, better enzymes are always sought. Should the reaction be part of a large scale industrial process, as in the instance of starch liquefaction, every item of expense falls under constant scrutiny. Accordingly, possible need to increase the dosage level of a relatively expensive enzyme about 50% for no reason other than to hydrolyze some small proportion carbohydrate component and thereby avoid appearance of excessively high sediment levels in the syrup is of real concern to the art, and may not be dismissed as inconsequential. As of the date hereof, the potential cost of excess enzyme to the high fructose syrup industry for using 150% or more of normal dosage levels of the alpha-amylase represents several million dollars per year, yet such cost might be less than the loss in yield and process expense costs entailed with acceptance of high sediment levels.

The normal dosage level range for starch liquefaction employing either the *Bacillus licheniformis* alpha-amylase at pH 6.0–6.5 or the *B. stearothermophilus* alpha-amylase at pH 5.5–6.0 is 40–80 NU/g DS (NOVO units per gram by dry substance starch). Above about a 100 NU/g DS dosage level for the latter enzyme, undue levels of sediment in the syrup are avoided.

Unfortunately, employment of such high dosage levels of the alpha-amylase does not offer compensating advantages, such as material reduction in the dosage levels of the saccharifying enzymes employed to convert the dextrin solution product of the starch liquefaction process into a glucose syrup.

In practice of this invention, normal enzyme dosage levels are employed, i.e., 40–80 NU/g DS, for the alpha-amylase mixture.

The starch liquefaction results are surprisingly good, being more than adequate. (The desired DE may be achieved more rapidly.) Since the alpha-amylase for

*Bacillus licheniformis* exhibits poor liquefaction results in the pH 5.5–6.0 range, and is known to generate some sediment when used in this pH range, such a full effect from the proportion of this enzyme in the mixture could not be expected.

Coupled with the more than adequate liquefaction results, sediment formation is avoided. It is noted that employment of the mixed alpha-amylases at 40–80 NU/g DS, e.g., at 37.5 NU/g DS for each alpha-amylase, results ultimately in good dextrose yield.

The plant operator must exercise judgment in establishing enzyme proportions and dosage, pH, and for that matter all operating parameters employed for the liquefaction.

For example, with the aforementioned embodiment mixture comprising about ⅔ the *Bacillus licheniformis* enzyme, ⅓ the *B. stearothermophilus* enzyme, test studies (see Ex. 7) (hereinafter) indicate that the operating pH level should be at the upper end of the 5.5–6.0 range. Operating at about pH 6.4 is conventional with the alpha-amylase from *Bacillus licheniformis* (e.g., TERMAMYL®). As might be expected, as good, and perhaps better results may be obtained with equal dosage of the ⅔/⅓ mixture at pH 6.3; 6.2, but operating at 6.2, 6.3 would not be an optimum use for the enzyme mixture since the principal objective of this invention is to reduce the pH (below pH 6.4) for liquefaction as much as is reasonable. More significant for the plant operator is that very good results are obtained at pH 5.9±0.1, i.e., the range of pH 5.8–6.0. Moreover, the good results obtained at pH 5.8–6.0 are with a somewhat lower enzyme dosage level (25% less in one plant trial, 15% in another plant trial). In addition, in one plant trial the ultimate yield of dextrose increased modestly but significantly (from about 95.3% to more than 96%) while the DP 2 side reaction product(s) decreased from about 2.7% to about 2.2%. Indeed, the ⅔/⅓ mixture tested out to be a more advantageous enzyme product than was expected by the inventors hereof.

For further understanding of this invention, the following specific Examples are presented.

The enzymes employed were commercially available enzymes. i.e., alpha-amylase from *Bacillus licheniformis* (TERMAMYL®) and alpha-amylase from *B. stearothermophilus* (THERMOLASE™), and also a *B. stearothermophilus* alpha-amylase (BPS-3) available only experimentally as of the date hereof.

Also employed (for saccharification purpose) was the usual dosage of a commercially available saccharifying enzyme mixture (DEXTROZYME™), which is a mixture of glucoamylase and pullulanase.

EXAMPLE 1

Jet cooking experiments listed in Table I below were carried out at 35% DS 105° C. jet temperature; secondary liquefaction for 60 and 90 minutes at 95° C.; $CaCl_2 \cdot 2H_2O$ was used to bring the concentration of $Ca^{++}$ to 40 ppm; NaCl was added to BPS-3 runs to match that of TERMAMYL® (final conductivity of the slurry was 290 μS). The starch used was a Staley corn starch (Lot F 29032 8521). D.E. and pH were measured.

TABLE I

CONDITIONS USED IN JET COOKING EXPERIMENTS

| Enzyme(s) | Liquefaction Dose (NU/g) | pH | Saccharification (pH 4.3, 60° C., 30–31% DS) |
|---|---|---|---|
| TERMAMYL® | 75 | 5.8 | After 60 and 90 minutes secondary liquefaction: DEXTROZYME® 150/50 L (AMPP 012) 0.18 Ag/g DS + 0.062 PUN/g; DS, DX and sediment were determined after 0, 18, 24, 32 and 48 hours of saccharification |
| BPS-3 | 75 | 5.8 | |
| BPS-3/ TERMAMYL® | 56.25/ 18.75 | 5.8 | |

The saccharification was carried out by standard practice in the high fructose syrup art of 48 hrs.@ 60° C., pH 4.3 with 1.2 L/TON DS of DEXTROZYME™ 150/50. Sediment levels were measured. The volume of sediment in ml per 100 ml of syrup was measured (% Vol/Vol). The results are tabulated below:

TABLE II

SEDIMENT FROM (DEXTROZYME ™) SACCHARIFICATIONS FROM TERMAMYL®, BPS-3 AND MIXTURES LIQUEFACTIONS

| Enzyme | Liquefaction Dose (NU/g DS) | pH | Time (Min) (Secondary) | Sediment % vol/vol Saccharification (hrs) | | | | |
|---|---|---|---|---|---|---|---|---|
| | | | | 0 | 18 | 24 | 32 | 48 |
| TERMAMYL® | 75 | 5.8 | 60 | <0.2 | 20 | 2.5 | 5 | 4.5 |
| | | | 90 | <0.2 | <0.2 | <0.2 | 4 | 3.5 |
| BPS-3 | 75 | 5.8 | 60 | <0.2 | 9 | 8 | 10 | 11.5 |
| | | | 90 | <0.2 | 8 | 8 | 10 | 11.5 |
| BPS-3/ TERMAMYL® | 56.25/ 18.75 | 5.8 | 60 | <0.2 | 6 | 6 | 8 | 8 |
| | | | 90 | <0.2 | 6 | 6 | 8 | 8 |

As shown by the results in Table III below, the dextrose yield data for all runs is acceptably high. The sediment level in the syrup made from the mixed enzyme liquefaction is significantly less than the sediment level from the BPS-3 catalyzed liquefaction.

TABLE III

DEXTROSE YIELD AS A FUNCTION OF TIME OF SACCHARIFICATION USING DEXTROZYME ™, AFTER LIQUEFACTION WITH TERMAMYL®, BPS-3, AND MIXTURES

| Enzyme | Liquefaction Dose (NU/g DS) | pH | Time (Min) (Secondary) | Dextrose Yield % Saccharification (hrs) | | | | |
|---|---|---|---|---|---|---|---|---|
| | | | | 18 | 24 | 28 | 32 | 48 |
| TERMAMYL® | 75 | 5.8 | 60 | 90.0 | 92.9 | — | 95.2 | 95.7 |
| | | | 90 | 89.0 | 92.3 | — | 94.8 | 95.4 |
| BPS-3 | 75 | 5.8 | 60 | 90.5 | 93.7 | — | 95.5 | 95.7 |
| | | | 90 | 89.5 | 93.1 | — | 95.2 | 95.7 |

TABLE III-continued

DEXTROSE YIELD AS A FUNCTION OF TIME OF SACCHARIFICATION USING DEXTROZYME ™, AFTER LIQUEFACTION WITH TERMAMYL ®, BPS-3, AND MIXTURES

| Liquefaction | | | | Dextrose Yield % | | | | |
|---|---|---|---|---|---|---|---|---|
| Enzyme | Dose (NU/g DS) | pH | Time (Min) (Secondary) | Saccharification (hrs) | | | | |
| | | | | 18 | 24 | 28 | 32 | 48 |
| BPS-3/ | 56.25/ | 5.8 | 60 | 91.0 | 93.7 | — | 95.0 | 96.2 |
| TERMAMYL ® | 18.75 | | 90 | 90.6 | 93.5 | — | 94.8 | 96.1 |

EXAMPLE 2

The liquefaction and saccharifying conditions of Example 1 were employed with a 50/50 mixture, and with each enzyme alone. The conditions and results are tabulated below.

TABLE IV

CONDITIONS USED IN JET COOKING EXPERIMENTS

| | Dose (NU/g DS) | pH |
|---|---|---|
| TERMAMYL ® | 75 | 5.8 |
| THERMOLASE ™ | 75 | 5.8 |
| THERMOLASE ™/ TERMAMYL ® | 37.5/ 37.5 | 5.8 |
| BPS-3/ TERMAMYL ® | 37.5/ 37.5 | 5.8 |

TABLE V

SEDIMENT FROM (DEXTROZYME ™) SACCHARIFICATIONS FROM TERMAMYL ®, BPS-3 AND MIXTURES LIQUEFACTIONS

| Liquefaction | | | | Sediment % vol/vol | | | | |
|---|---|---|---|---|---|---|---|---|
| Enzyme | Dose (NU/g DS) | pH | Time (Min) (Secondary) | Saccharification (hrs) | | | | |
| | | | | 0 | 18 | 24 | 32 | 48 |
| TERMAMYL ® | 75 | 5.8 | 60 | — | <0.2 | 3.5 | 5 | 5 |
| | | | 90 | — | <0.2 | 3.5 | 5 | 4.5 |
| THERMOLASE ™ | 75 | 5.8 | 60 | — | 10 | 12 | 15 | 15 |
| | | | 90 | — | 12 | 12 | 15 | 15 |
| THERMOLASE ™/ TERMAMYL ® | 37.5/ 37.5 | 5.8 | 60 | — | 6.5 | 7 | 6 | 5 |
| | | | 90 | — | 6.5 | 6 | 5 | 4 |
| BPS-3/ TERMAMYL ® | 37.5/ 37.5 | 5.8 | 60 | — | 6 | 5 | 8 | 4.5 |
| | | | 90 | — | 6 | 5 | 8 | 4.5 |

TABLE VI

DEXTROSE YIELD AS A FUNCTION OF TIME OF SACCHARIFICATION USING DEXTROZYME ™, AFTER LIQUEFACTION WITH TERMAMYL ®, BPS-3, AND MIXTURES

| Liquefaction | | | | Dextrose Yield % | | | | |
|---|---|---|---|---|---|---|---|---|
| Enzyme | Dose (NU/g DS) | pH | Time (Min) (Secondary) | Saccharification (hrs) | | | | |
| | | | | 0 | 18 | 24 | 32 | 48 |
| TERMAMYL ® | 75 | 5.8 | 60 | 90.0 | 92.9 | — | 95.2 | 95.7 |
| | | | 90 | 89.0 | 92.3 | — | 94.8 | 95.4 |
| BPS-3/ TERMAMYL ® | 37.5/ 37.5 | 5.8 | 60 | — | 93.3 | 94.2 | 95.3 | 96.0 |
| | | | 90 | 89.4 | 92.4 | 93.5 | 94.8 | 95.8 |
| THERMOLASE ™ | 75 | 5.8 | 60 | 90.6 | 93.6 | 94.9 | 95.4 | 96.1 |
| | | | 90 | 87.3 | 93.0 | 94.6 | 95.2 | 96.1 |
| THERMOLASE ™/ TERMAMYL ® | 37.5/ 37.5 | 5.8 | 60 | 91.3 | 93.4 | 94.6 | 95.3 | 96.2 |
| | | | 90 | — | 93.0 | 94.3 | 95.0 | 96.1 |

EXAMPLE 3

The liquefaction and saccharification of Example 2 was repeated for the BPS-3 with 90 minutes of saccharification and filtration data was obtained. The saccharification results data (not reproduced) was consistent with the data provided in Example 2.

The filtration rates for the syrups were ascertained by the filter test leaf method, results being reported as the average of about 20 filtration cycles in ml cycle. The proportion of syrup insolubles was measured as percent by weight of the DS. The results are tabulated below.

TABLE VII

FILTERABILITY OF DEXTROSE SYRUPS VS. SEDIMENT AND INSOLUBLES

| | Sediment % Vol/Vol | Filtration Rate (ml/cycle) | Insolubles % of DS |
|---|---|---|---|
| TERMAMYL ® | 4 | 110 | 1.2 |
| TERMAMYL ® | 5 | 94 | 1.3 |
| BPS-3 | 12 | 70 | 3.4 |
| TERMAMYL ®/ BPS-3 | 4 | 99 | 1.5 |

EXAMPLE 4

The study of Examples 1 and 2 was repeated using a liquefaction pH of pH 5.5 with the BPS-3. The results are tabulated below.

TABLE VIII

CONDITIONS USED IN JET COOKING EXPERIMENTS

| Liquefaction | | | |
|---|---|---|---|
| Enzyme(s) | Dose (NU/g) | pH | Saccharification (pH 4.3, 60° C., 30–31% DS) |
| BPS-3/ TERMAMYL ® | 37.5/ 37.5 | 5.5 | After 60 and 90 minutes secondary liquefaction: Dextrose yield and sediment were determined |
| BPS-3 | 100 | 5.5 | after 48 hours of using |

TABLE VIII-continued

CONDITIONS USED IN JET COOKING EXPERIMENTS

| Enzyme(s) | Liquefaction Dose (NU/g) | pH | Saccharification (pH 4.3, 60° C., 30-31% DS) |
|---|---|---|---|
| | | | saccharification using DEXTROZYME ™ 150/50 |

TABLE X

SEDIMENT FROM (DEXTROZYME ™) SACCHARIFICATIONS FROM TERMAMYL ®, BPS-3 AND MIXTURES LIQUEFACTIONS

| | Liquefaction | | | Sediment % vol/vol | | | | |
|---|---|---|---|---|---|---|---|---|
| | Dose | | Time (Min) | | Saccharification (hrs) | | | |
| Enzyme | (NU/g DS) | pH | (Secondary) | 0 | 18 | 24 | 32 | 48 |
| BPS-3/ | 37.5/ | 5.5 | 60 | — | — | — | — | 8.0 |
| TER-MAMYL ® | 37.5 | | 90 | — | — | — | — | 6.5 |
| BPS-3 | 100 | 5.5 | 60 | — | — | — | — | 6.5 |
| | | | 90 | — | — | — | — | 50.0 |

TABLE XI

DEXTROSE YIELD AS A FUNCTION OF TIME OF SACCHARIFICATION USING DEXTROZYME ™, AFTER LIQUEFACTION WITH TERMAMYL ®, BPS-3 AND MIXTURES

| | Liquefaction | | | Dextrose Yield % | | | | |
|---|---|---|---|---|---|---|---|---|
| | Dose | | Time (Min) | | Saccharification (hrs) | | | |
| Enzyme | (NU/g DS) | pH | (Secondary) | 0 | 18 | 24 | 32 | 48 |
| BPS-3/ | 37.5/ | 5.5 | 60 | — | — | — | — | 96.1 |
| TER-MAMYL ® | 37.5 | | 90 | — | — | — | — | 96.1 |
| BPS-3 | 100 | 5.5 | 60 | — | — | — | — | 96.1 |
| | | | 90 | — | — | — | — | 96.0 |

Example 4 demonstrates that the advantages to practice of this invention are reduced when liquefaction is carried out at pH 5.5.

EXAMPLE 5

A split enzyme dose test was conducted following the operating conditions of Example 1 to ascertain whether sequential addition of the enzyme reduces sediment. The *B. stearothermophilus* enzyme, which was BPS-3, was employed alone at 50 NU/g DS for the primary liquefaction. Upon commencement of a 90 minute secondary liquefaction, an additional 25 NU/g DS either of TERMAMYL ® or of BPS-3 was added. Tabulated below are: sediment volumes found in the ultimate syrup; DE after secondary liquefaction; and, the final DX dextrose content in the syrup.

| Added Enzyme | Sediment % Vol/Vol | D.E. | Final DX |
|---|---|---|---|
| 0 | 40 | 10.8 | 96 |
| 25 BPS-3 | 25 | 14.6 | 96 |
| 25 TERMAMYL ® | 25 | 12.9 | 95.5 |

Although the DE and DX results are all acceptable, the sediment levels are all quite excessive.

The D.E. rate data for the secondary liquefaction of the test studies described as the above Examples indicates that the secondary liquefaction proceeds more rapidly with the enzyme mixtures than with either enzyme alone. Thus, if a particular target DE is sought, greater throughput from a given liquefaction installation becomes possible. A limiting parameter for many high fructose producer facilities is the capacity of the secondary liquefaction step. Practice of this invention may be particularly advantageous during periods of peak seasonal demand for high fructose syrups from any such capacity limited facility.

EXAMPLE 6

Liquefaction at pH 5.5 with an α-amylase composition containing 50% TERMAMYL ® α-amylase by activity in NU.

Some of the experiments in Example 2 were repeated at pH 5.5 instead of 5.8. The results are tabulated below.

TABLE XII

| α-amylase | Dose NU/g | pH | 2nd liquefact. minutes | Sediment % | DX |
|---|---|---|---|---|---|
| THERMOLASE ™ | 75 | 5.5 | 60 | 9 | 96.2 |
| | | | 90 | 7.5 | 96.3 |
| THERMOLASE ™ / TERMAMYL ® | 37.5/ 37.5 | 5.5 | 60 | 4.5 | 96.2 |
| | | | 90 | 4.0 | 96.2 |

Approximately half the amount of sediment was observed with the mixture at both secondary liquefaction times.

EXAMPLE 7

Two large scale trials, i.e., plant trials were carried out in which a mixed enzyme product (SP 404) ⅔ TERMAMYL ™, ⅓ THERMOLASE ™ by activity was substituted for TERMAMYL during otherwise normal operation of the plant. On successive days the pH of the liquefaction was reduced, and during the course of the plant trials, enzyme dosage was reduced (gradually). In both plant trials, the optimum pH for liquefaction was found to be pH 5.9±0.1. In both plant trials the enzyme dosage could be reduced yet produce liquefaction results comparable to result with TERMAMYL ™, but with differences installation to installation, i.e., 15% in one installation, about 25% in the other installation.

In one installation, the % dextrose and the % DP 2 (disaccharides) in the saccharified glucose syrup was being monitored daily. Over the course of the trial, the content of DP 2 decreased from about 2.6% to about 2.2% and the dextrose content increased from an average of about 95.3% to as high as 96.1%. These advantageous results are attributed to reduced (or eliminated) formation of the maltulose which is formed when liquefaction pH exceeds pH 6.0.

Below tabulated is the data obtained from both installation trials.

TABLE XIII

| Enzyme | pH | NU/gds | Sediment | Final DE |
|---|---|---|---|---|
| T-120* | 6.4 | 69 | 1.3 | 9.7 |
| SP-404** | 6.2 | 69 | 1.3 | 14.2 |
| SP-404 | 6.0 | 67 | 1.4 | 15.7 |
| SP-404 | 5.8 | 65 | 1.3 | 10.3 |

*Termamyl 120
**Amylase Mixture

TABLE XIV

| Enzyme | pH | NU/gds | Sediment | Final DE |
|---|---|---|---|---|
| T-120 | 6.4 | 75 | 1.75 | 9.9 |
|  | 6.4 | 75 | 1.75 | 9.9 |
| SP-404 | 6.3 | 75 | 1.40 | 13.0 |
| SP-404 | 6.0 | 75 | 1.40 | 12.1 |
| SP-404 | 5.8 | 75 | 1.40 | 12.7 |
| SP-404 | 6.0 | 65 | 1.60 | 11.4 |
| SP-404 | 5.9 | 62 | No Data | 10.7 |

We claim:

1. A mixed enzyme product comprising a mixture of the alpha-amylase from *Bacillus licheniformis* and the alpha-amylase from *B. stearothermophilus*, said mixture containing from 25%–90% by activity as NU/g DS of the *Bacillus licheniformis* enzyme.

2. In a process for liquefying starch or starchy grains which comprises subjecting an aqueous slurry of 32–38% dry substance by weight and an alpha-amylase in dosage of from 20–80 NU/g dry starch to jet cooking at a temperature in the range of 100° C.–115° C. for 1–60 minutes, followed by reducing temperature to a temperature in the range of 90° C.–100° C. for 30–180 minutes after which so liquefied starch is stable against retrogradation, the improvement which comprises conducting said liquefaction in the range of about pH 5.5–6.2 with an enzyme mixture of the alpha-amylase from *Bacillus licheniformis* and the alpha-amylase from *B. stearothermophilus* containing from 10%–90% by activity as NU/g DS of the *Bacillus licheniformis* enzyme.

3. A mixed enzyme product as in claim 1 containing from 25–75% of the *Bacillus licheniformis* enzyme.

4. A liquefying process as in claim 2 which further comprises liquefying with an enzyme mixture containing from 25–90% of the *Bacillus licheniformis* enzyme.

5. A liquefying process as in claim 2 which further comprises liquefying with an enzyme mixture containing from 25–75% of the *Bacillus licheniformis* enzyme.

6. A liquefying process as in claim 2 which further comprises liquefying with an enzyme mixture containing about ⅔ thereof of the *Bacillus licheniformis* enzyme at a pH in the range of about pH 5.8–6.0.

7. A mixed enzyme product comprising a mixture of the alpha-amylase from *Bacillus licheniformis* and the alpha-amylase from *B. stearothermophilus*, said mixture containing about ⅔ by activity as NU/g DS of the *Bacillus licheniformis* enzyme.

* * * * *